United States Patent
Kim et al.

(10) Patent No.: US 10,548,556 B2
(45) Date of Patent: Feb. 4, 2020

(54) METHOD FOR REGISTERING MEDICAL IMAGES

(71) Applicant: SAMSUNG ELECTRONICS CO., LTD., Suwon-si (KR)

(72) Inventors: Jungbae Kim, Seoul (KR); Youngtaek Oh, Seoul (KR); Youngkyoo Hwang, Seoul (KR); Joonho Seo, Seoul (KR); Wonchul Bang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1015 days.

(21) Appl. No.: 14/707,099

(22) Filed: May 8, 2015

(65) Prior Publication Data

US 2015/0320400 A1 Nov. 12, 2015

(30) Foreign Application Priority Data

May 12, 2014 (KR) .................. 10-2014-0056573

(51) Int. Cl.
*A61B 5/00* (2006.01)
*A61B 6/00* (2006.01)
(Continued)

(52) U.S. Cl.
CPC .......... *A61B 6/5247* (2013.01); *A61B 8/4245* (2013.01); *A61B 8/5261* (2013.01);
(Continued)

(58) Field of Classification Search
CPC . G06T 2207/10081; G06T 2207/10088; G06T 2207/10101; G06T 2207/10104;
(Continued)

(56) References Cited

U.S. PATENT DOCUMENTS 8,340,374 B2 12/2012 Yamagata
8,355,775 B2 1/2013 Oshiki et al.
(Continued)

FOREIGN PATENT DOCUMENTS

CN 102169578 A 8/2011
CN 102663803 A 9/2012
(Continued)

OTHER PUBLICATIONS

Chiu, et al.; "Characterization of Carotid Plaques on 3-Dimensional Ultrasound Imaging by Registration With Multicontrast Magnetic Resonance Imaging", Journal of the American Institute of Ultrasound in Medicine, Oct. 2012, 14 pages total.
(Continued)

*Primary Examiner* — Ruth S Smith
(74) *Attorney, Agent, or Firm* — Sughrue Mion, PLLC

(57) ABSTRACT

Provided are a method and apparatus for registering medical images. The method includes: setting, as a reference, axis an axis of a probe that is disposed to be parallel to an axis of an object; extracting a first sub-object from a first medical image that is obtained by using the probe; extracting a second sub-object from a second medical image that has a modality different from a modality of the first medical image; and registering the first medical image and the second medical image by aligning the first sub-object and the second sub-object about the reference axis.

9 Claims, 6 Drawing Sheets

(51) Int. Cl.
*A61B 8/00* (2006.01)
*G06T 3/00* (2006.01)
*A61B 8/08* (2006.01)
*A61B 6/03* (2006.01)
*A61B 8/14* (2006.01)

(52) U.S. Cl.
CPC .......... *G06T 3/0068* (2013.01); *A61B 5/0066* (2013.01); *A61B 6/032* (2013.01); *A61B 6/037* (2013.01); *A61B 8/14* (2013.01); *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/10132* (2013.01); *G06T 2207/30004* (2013.01)

(58) Field of Classification Search
CPC . G06T 2207/10108; G06T 2207/10116; G06T 2207/10132; G06T 2207/30172; G06T 3/0068; G06T 2207/30004; G06T 7/33; G06T 7/337; G06T 7/00; G06T 3/00; A61B 6/463; A61B 6/5223; A61B 6/5247; A61B 8/4254; A61B 8/463; A61B 8/5261; A61B 5/0066; A61B 8/14; A61B 8/4245; A61B 5/0035; A61B 8/08; A61B 5/055; A61B 8/00; A61B 6/032; A61B 6/037

USPC .......................................... 600/407; 382/131
See application file for complete search history.

(56) References Cited

U.S. PATENT DOCUMENTS

| 8,447,383 | B2 | 5/2013 | Hyun et al. |
| 2010/0286517 | A1 | 11/2010 | Kamen et al. |
| 2011/0160566 | A1 | 6/2011 | Petropoulos et al. |
| 2013/0053679 | A1 | 2/2013 | Owen |
| 2014/0193053 | A1* | 7/2014 | Kadoury ............... G06T 11/008 382/131 |

FOREIGN PATENT DOCUMENTS

| KR | 10-2007-0110965 A | 11/2007 |
| KR | 10-1121286 B1 | 3/2012 |
| WO | 2012/117381 A1 | 9/2012 |
| WO | 2012117381 A1 | 9/2012 |

OTHER PUBLICATIONS

Communication dated Oct. 6, 2015, issued by the European Patent Office in counterpart European Application No. 15167374.6.
Communication dated Feb. 26, 2019, from the State Intellectual Property Office of People's Republic of China in counterpart Application No. 201510027082.3.

* cited by examiner

METHOD FOR REGISTERING MEDICAL IMAGES

CROSS-REFERENCE TO RELATED APPLICATIONS

This application claims the benefit of Korean Patent Application No. 10-2014-0056573, filed on May 12, 2014, in the Korean Intellectual Property Office, the disclosure of which is incorporated herein in its entirety by reference.

BACKGROUND

1. Field

The exemplary embodiments relate to methods and apparatuses for matching medical images having different modalities.

2. Description of the Related Art

With recent developments in medical technology, high resolution medical images may be obtained. As a medical device may be finely manipulated, a method of forming a small puncture hole in the skin, directly inserting a catheter or a medical needle into a blood vessel or a desired body part, and providing treatment while observing the interior of the body by using a medical imaging device has been developed. The method is referred to as a "treatment method using an image" or an "interventional imaging method".

A practitioner recognizes a location of an organ or a lesion by using an image. In addition, since a patient breathes or moves, the practitioner has to recognize a change in position according to the breathing or movement. Accordingly, the practitioner has to provide treatment by accurately and quickly recognizing the breathing or the movement based on an image in real time. In this case, however, it is not easy to recognize with the naked eye a shape of the organ or the lesion in an ultrasound image that may be obtained in real time.

A magnetic resonance (MR) or computed tomography (CT) image, unlike the ultrasound image, enables the practitioner to clearly identify the organ or the lesion. However, since the MR or CT image may not be obtained in real time during medical treatment, the MR or CT image fails to reflect the patient's breathing or movement that occurs during the medical treatment.

Accordingly, it is necessary to register a first image that is captured in real time with a second image that has a modality different from a modality of the first image. When a plurality of images having different modalities is to be registered, feature points may be extracted from the images and may be registered. In this case, however, it may be difficult to perform the registration according to quality of the images.

SUMMARY

Provided are methods and apparatuses for registering a plurality of medical images having different modalities by using a sensor.

Additional aspects will be set forth in part in the description which follows and, in part, will be apparent from the description, or may be learned by practice of the presented exemplary embodiments.

According to an aspect of an exemplary embodiment, there is provided a method of registering medical images including: setting, as a reference axis, an axis of a probe that is disposed to be parallel to an axis of an object; extracting a first sub-object from a first medical image that is obtained by using the probe; extracting a second sub-object from a second medical image that has a modality different from a modality of the first medical image; and registering the first medical image and the second medical image by aligning the first sub-object and the second sub-object about the reference axis.

The axis of the object may be parallel to a coordinate axis of the second medical image.

The registering may include calculating a conversion relationship between a coordinate system of the first medical image and a coordinate system of the second medical image based on aligning the first sub-object and the second sub-object.

The calculating of the conversion relationship may include rotating a coordinate axis of the first medical image to be parallel to the reference axis and moving the rotated coordinate axis of the first medical image to align the first sub-object and the second sub-object.

The method may further include extracting from the second medical image a cross-section of the second medical image corresponding to a cross-section of the first medical image based on the conversion relationship.

The extracting of the cross-section of the second medical image corresponding to the cross-section of the first medical image may include: converting coordinate information about the cross-section of the first medical image into coordinate information of the second medical image to thereby generate conversion-obtained coordinate information; and extracting from the second medical image the cross-section of the second medical image having the conversion-obtained coordinate information.

The coordinate information about the cross-section of the first medical image may correspond to coordinate information of the probe in a one-to-one manner.

The method may further include displaying both the cross-section of the first medical image and the cross-section of the second medical image.

The cross-section of the first medical image and the cross-section of the second medical image may correspond to a same view of the object.

The aligning may include matching the first sub-object and the second sub-object, when the first sub-object and the second sub-object represent a same physical object.

The aligning may include matching a geometric arrangement between the first sub-object and the second sub-object with a geometric arrangement that is previously stored, when the first sub-object and the second sub-object represent different physical objects from each other.

The first medical image may be an image that is captured in real time, and the second medical image may be an image that is previously captured.

The first medical image may be at least one of an ultrasound image and an optical coherence tomography (OCT) image, and the second medical image may be at least one of a magnetic resonance (MR) image, a computed tomography (CT) image, a position emission tomography (PET) image, a single-photon emission computed tomography (SPECT) image, and an X-ray image.

According to another aspect of an exemplary embodiment, there is provided a medical imaging apparatus including: a probe configured to obtain a first medical image of an object; and an image processor configured to set, as a reference axis, an axis of the probe that is disposed to be parallel to an axis of the object, extract a first sub-object from the first medical image, extract a second sub-object from a second medical image that has a modality different from a modality of the first medical image, and register the first medical image and the second medical image by aligning the first sub-object and the second sub-object using the reference axis.

The axis of the object may be parallel to a coordinate axis of the second medical image.

The image processor may be configured to calculate a conversion relationship between a coordinate system of the first medical image and a coordinate system of the second medical image based on aligning the first sub-object and the second sub-object.

The image processor may be configured to calculate the conversion relationship by rotating a coordinate axis of the first medical image to be parallel to the reference axis and moving the rotated coordinate axis of the first medical image to align the first sub-object and the second sub-object.

The image processor may be configured to extract, from the second medical image, a cross-section of the second medical image corresponding to a cross-section of the first medical image based on the conversion relationship.

The image processor may be configured to extract, from the second medical image, the cross-section of the second medical image corresponding to the cross-section of the first medical image by converting coordinate information about the cross-section of the first medical image into coordinate information of the second medical image to thereby generate conversion-obtained coordinate information, and extract, from the second medical image, the cross-section of the second medical image having the conversion-obtained coordinate information.

The medical imaging apparatus may further include a sensor configured to detect at least one of a location of the probe and an orientation of the probe with respect to the object, and the coordinate information about the cross-section of the first medical image may correspond in a one-to-one manner to coordinate information of the probe that indicates at least one of the location of the probe and the orientation of the probe.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
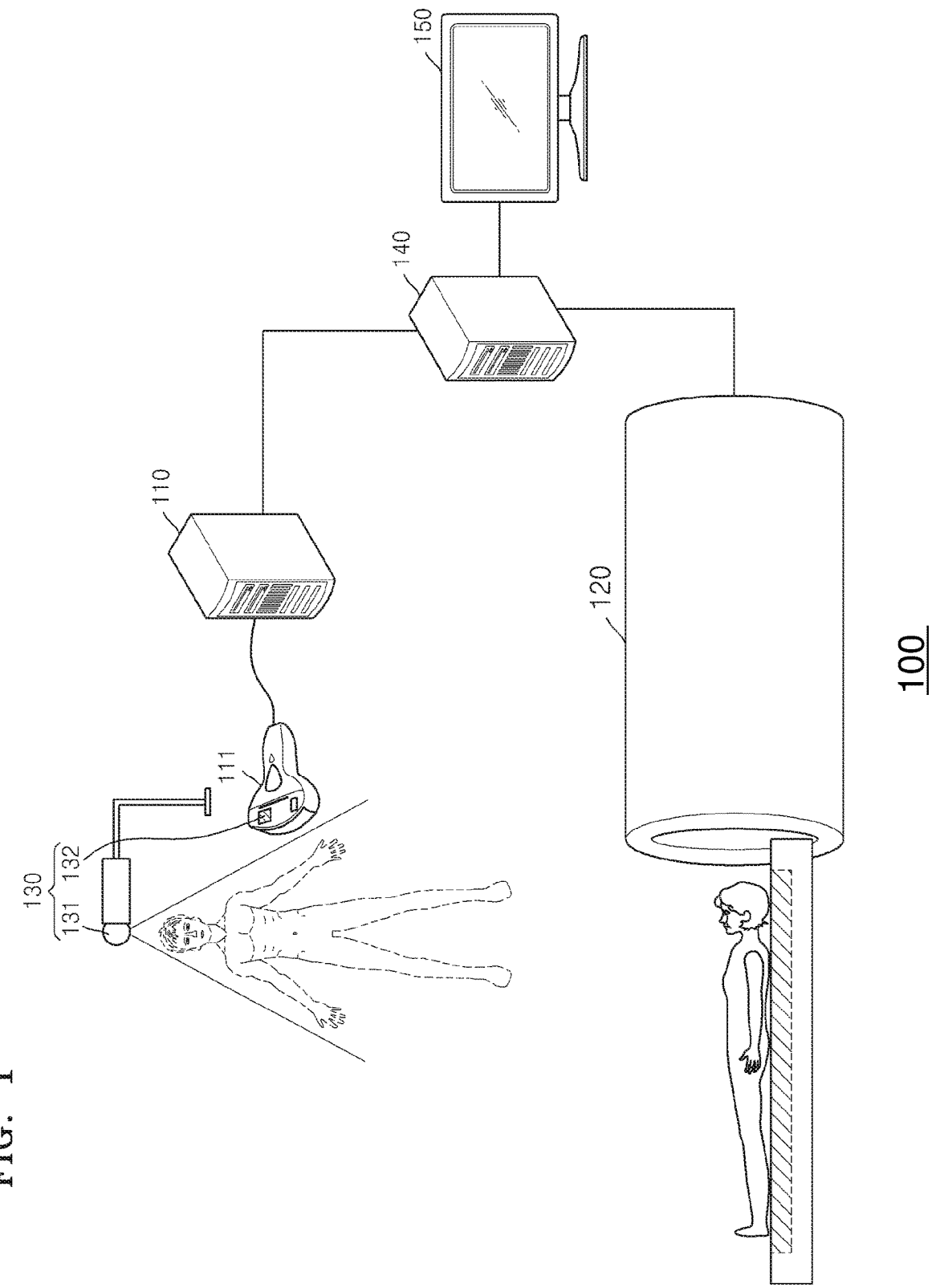
FIG. 1 is a view illustrating a medical imaging system according to an exemplary embodiment.

Exemplary embodiments will be described more fully hereinafter with reference to the accompanying drawings, in which exemplary embodiments are shown. In the drawings, like elements are denoted by like reference numerals, and a repeated explanation thereof will not be given.

The term "object" used herein may include a human, an animal, or a body part of a human or an animal. For example, the object may include an organ such as the liver, heart, womb, brain, breast, or stomach, or a blood vessel. Also, the term "user" used herein may refer to, but is not limited to, a medical expert such as a doctor, a nurse, a clinical pathologist, a medical image expert, or an engineer who repairs a medical device.

As used herein, the term "and/or" includes any and all combinations of one or more of the associated listed items. Expressions such as "at least one of," when preceding a list of elements, modify the entire list of elements and do not modify the individual elements of the list.

FIG. 1 is a view illustrating a medical imaging system 100 according to an exemplary embodiment. Referring to FIG. 1, the medical imaging system 100 includes a first medical apparatus 110, a second medical apparatus 120, a detection apparatus 130, a registration apparatus 140, and a display apparatus 150.

The first medical apparatus 110 and the second medical apparatus 120 respectively generate a first medical image and a second medical image and respectively provide the first medical image and the second medical image to the registration apparatus 140. The first medical image and the second medical image have different modalities. That is, according to an exemplary embodiment, the first medical image and the second medical image may have different generation methods and principles. The registration apparatus 140 receives the first medical image and the second medical image, and registers the first medical image and the second medical image having different modalities. The first medical image and second medical image registered by the registration apparatus 140 may be displayed on the display apparatus 150.

The first medical apparatus 110 provides in real time the first medical image of a volume of interest (VOI) of an object. For example, when an organ is deformed or displaced due to the object's physical activity, the first medical image is changed in real time. However, all organs and lesions may not be clearly observed in the first medical image and it may be difficult to recognize the deformation and the displacement of the organ by using only the first medical image.

According to an exemplary embodiment, the first medical apparatus 110 may be an ultrasonography machine that generates an image in real time during interventional medical treatment performed on a patient. However, the exemplary embodiments are not limited thereto, and the first medical apparatus 110 may be any type of other medical apparatus, such as an optical coherence tomography (OCT) apparatus that provides an image in real time.

When the first medical apparatus 110 is implemented as an ultrasonography machine, the first medical apparatus 110 generates an ultrasound image by emitting ultrasound to the object by using a probe 111 and detecting reflected ultrasound. The probe 111 may generally include a piezoelectric transducer. However, the exemplary embodiments are not limited thereto. The probe 111 may include at least one of a capacitive micromachined ultrasonic transducer (cMUT) that mutually converts ultrasound and an electrical signal by using a change in capacitance, a magnetic micromachined ultrasonic transducer (mMUT) that mutually converts ultrasound and an electrical signal by using a change in a magnetic field, and an optical ultrasonic detector that mutually converts ultrasound and an electrical signal by using a change in optical properties.

When ultrasound is applied at tens to hundreds of MHz from the probe 111 to a specific portion in the patient's body, the ultrasound is partially reflected from layers between various different tissues. The ultrasound is reflected from sub-objects having different densities in the patient's body, for example, blood cells in blood plasma or small structures in organs.

The reflected ultrasound vibrates a transducer of the probe 111, and the transducer outputs electrical pulses according to the vibration. The electrical pulses are converted into an image. When sub-objects have different ultrasound reflection characteristics, the sub-objects may be displayed with different brightness values in an ultrasound image in a B mode.

The second medical apparatus 120 generates the second medical image of the VOI of the object in non-real time. Considering the non-real time characteristics of the second medical apparatus 120, the second medical image may be previously captured before medical treatment.

For example, the second medical apparatus 120 may be any one of a computed tomography (CT) apparatus, a magnetic resonance (MR) imaging apparatus, an X-ray imaging apparatus, a single-photon emission computed tomography (SPECT) apparatus, and a position emission tomography (PET) apparatus. For convenience of explanation, the following description assumes that the second medical image is an MR or CT image, but the exemplary embodiments are not limited thereto.

In the CT image or MR image generated by the second medical apparatus 120, a location of an organ or a location of a lesion may be clearly distinguished. However, when the patient breaths or moves, the organ may be deformed or displaced. In this case, the CT or MR image may not reflect in real time the deformation or displacement of the organ as the patient breathes or moves.

The reason why the second medical apparatus 120 may not output an image in real time is that in the case of the CT image, since the CT image is captured by using radiation and thus there is a risk that the patient and a practitioner are exposed to the radiation for a long time, short image-capturing is recommended. Further, in the case of the MR image, it takes a long time to capture the MR image. In general, the CT image is captured when the patient temporarily stops breathing, for example, inhales deeply.

A medical image generated by the first medical apparatus 110 or the second medical apparatus 120 may be a three-dimensional (3D) image that is generated by stacking two-dimensional (2D) cross-sections. For example, the first medical apparatus 110 may generate a 2D cross-section, and may generate a 3D image by hand-sweeping or wobbling the probe 111 that is a 2D array probe. The second medical apparatus 120 captures a plurality of cross-sections by changing a location or an orientation of the cross-section. When the cross-sections are stacked, 3D volume image data three-dimensionally representing a specific portion of the patient's body may be generated. A method of generating 3D volume image data by stacking cross-sections is referred to as multiplanar reconstruction (MPR). The second medical image may be an image having a contrast which is enhanced in order to increase the brightness of the patient's organ of interest. For convenience of explanation, the following will be described on the assumption that the first medical image and the second medical image are 3D images.

The detection apparatus 130 may detect a movement of the probe 111 by detecting at least one selected from a location and an orientation of the probe 111. The detection apparatus 130 may include a magnetic field generator 131 and a sensor 132 that detects a change in a magnetic field. The magnetic field generator 131 may be fixed to a specific portion of the first medical apparatus 110, and the sensor 132 may be provided on the probe 111. Accordingly, the detection apparatus 130 may detect at least one selected from a location and an orientation of the probe 111 based on a positional relationship between the sensor 132 and the magnetic field generator 131. In addition, the detection apparatus 130 may include at least one of an optical sensor, an acceleration sensor, or a gyro sensor for detecting at least one selected from a location and an orientation of the probe 111. The detection apparatus 130 may calculate at least one selected from a location and an orientation of the probe 111 as coordinate information in a coordinate system used by the detection apparatus 130.

The registration apparatus 140 registers the first medical image that is obtained from the first medical apparatus and the second medical image that is obtained from the second medical apparatus 120. The registration of the first and second medical images may include matching a coordinate system used in the first medical image and a coordinate system used in the second medical image. A movement of the probe 111 and a cross-section of the first medical image may correspond to each other in a one-to-one manner. For a user, it may be easier to control a movement of the probe 111 than to control the first medical image. Accordingly, the registration of the first and second medical images may be performed by using orientation information of the probe 111 and location information of sub-objects that are included in the first and second medical images. In this case, less anatomical knowledge about the object is requested than when image registration is performed only based on a movement of the probe 111, that is, the detection apparatus 130. Also, in this case, there is a smaller possibility of registration errors than when image registration is performed based on a sub-object in an image.

According to an exemplary embodiment, a registered image may be an image obtained by fusing the first medical image and the second medical image. According to another exemplary embodiment, the registered image may be an image obtained by arranging the first medical image and the second medical image in parallel at the same observation time. The registered image is displayed on the display apparatus 150.

Although the first medical apparatus 110, the detection apparatus 130, the registration apparatus 140, and the display apparatus 150 are shown as being independent apparatuses in FIG. 1 for convenience of explanation, it is understood that the first medical apparatus 110, the detection apparatus 130, the registration apparatus 140, and the display apparatus 150 may be integrated into a single apparatus or other combinations of apparatuses. When the first medical apparatus 110, the detection apparatus 130, the registration apparatus 140, and the display apparatus 150 are integrated into a single apparatus, the detection apparatus 130 may be referred to as a detection unit (e.g., detector), the registration apparatus 140 may be referred to as an image processing unit (e.g., image processor), and the display apparatus 150 may be referred to as a display unit (e.g., display).

In order to easily register the first and second medical images, an orientation of the probe 111 may be initialized. An axis of the probe 111 may be divided into at least two axes that orthogonally intersect each other about the probe 111, and may be the same as a coordinate axis of a cross-section that is obtained by using the probe 111. For example, the two axes of the probe 111 may be a first axis that corresponds to a direction in which ultrasound travels and a second axis that orthogonally intersects the first axis. Also, an axis of the object may be divided into at least two axes that orthogonally intersect each other about the object, and may be the same as a coordinate axis of the second medical image. A plane including the two axes of the object may be divided into a sagittal plane, a coronal plane, and a transverse plane, and at least one of the sagittal plane, the coronal plane, and the transverse plane may be considered a reference plane.

Figure 2:
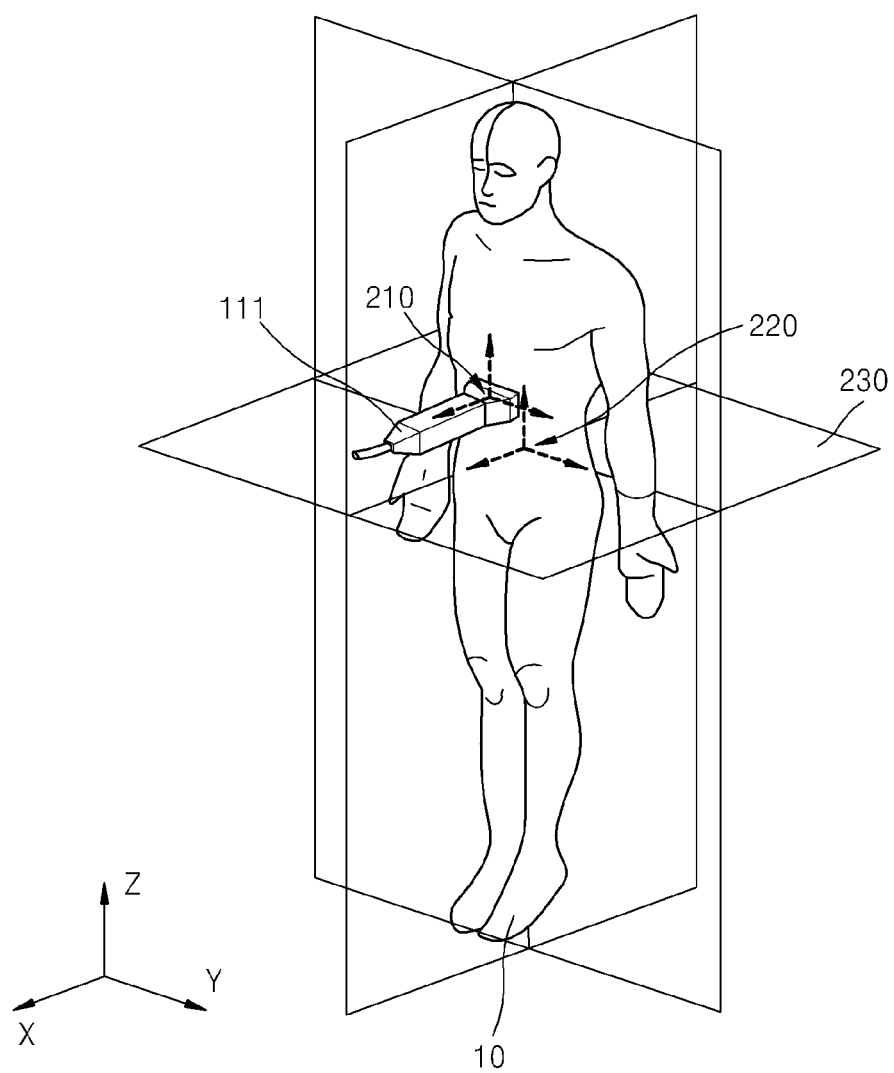
FIG. 2 is a reference view for explaining a method of initializing a probe, according to an exemplary embodiment.

FIG. 2 is a reference view for explaining a method of initializing the probe 111, according to an exemplary embodiment. As shown in FIG. 2, the user may dispose an axis 210 of the probe 111 to be parallel to an axis 220 of an object 10. For example, when two axes of the probe 111 are disposed to be parallel to a transverse plane 230 of the object 10, an orientation of the probe 111 may be initialized or the axis 210 of the probe 111 may become a reference axis. When the axis 210 of the probe 111 is disposed to be parallel to the axis 220 of the object 10, the detection apparatus 130 may set the axis 210 of the probe 111 as a coordinate axis used by the detection apparatus 130. Alternatively, when the axis 210 of the probe 111 is disposed to be parallel to the axis 220 of the object 10, the registration apparatus 140 may set a coordinate axis of a cross-section of the first medical image that is obtained by using the probe 111 as a coordinate axis of the first medical image.

Figure 3:
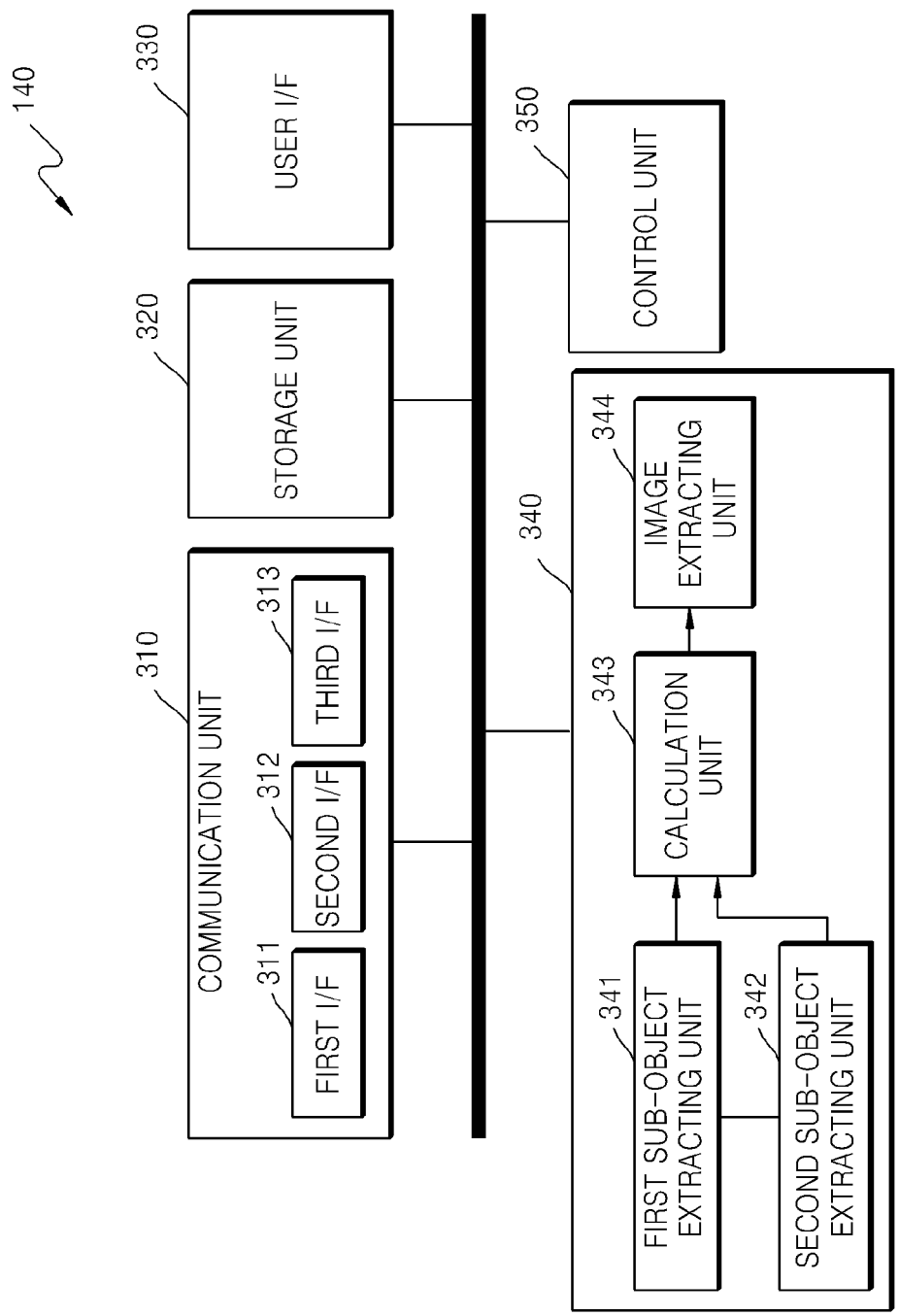
FIG. 3 is a block diagram illustrating a registration apparatus of FIG. 1.

FIG. 3 is a block diagram illustrating the registration apparatus 140 of FIG. 1, according to an exemplary embodiment. Referring to FIG. 3, the registration apparatus 140 may include a communication unit 310 (e.g., communicator), a storage unit 320 (e.g., storage), a user interface 330, an image processing unit 340 (e.g., image processor), and a control unit 350 (e.g., controller). However, according to other exemplary embodiments, the registration apparatus 140 may omit certain of the elements illustrated in FIG. 3, or may further include general-purpose elements instead of or in addition to the elements illustrated in FIG. 3.

The communication unit 310 may receive a first medical image and a second medical image respectively from the first medical apparatus 110 and the second medical apparatus 120, and may receive at least one from among location information and orientation information of the probe 111 from the detection apparatus 130. The communication unit 310 includes first and second interfaces 311 and 312 for respectively obtaining the first medical image and the second medical image from the first medical apparatus 110 and the second medical apparatus 120. The first interface 311 and the second interface 312 are interfaces that are directly or indirectly connected to the first medical apparatus 110 and the second medical apparatus 120 respectively.

The first interface 311 may obtain in real time the first medical image that is generated by the first medical apparatus 110. The second interface 312 may be directly connected to the second medical apparatus 120 to obtain the second medical image that is previously generated by the second medical apparatus 120 before medical treatment. Alternatively, the second interface 312 may obtain the second medical image by use of another external storage medium (such as a universal serial bus (USB), a compact disc (CD), or a digital versatile disc (DVD)) or via a network (e.g., a local area network (LAN) or the Internet). The communication unit 310 may store the obtained second medical image in the storage unit 320. A third interface 313 may receive orientation information of the probe 111 from the detection apparatus 130. Although, according to an exemplary embodiment, the first medical image and the orientation information of the probe 111 are received by different interfaces, the exemplary embodiments are not limited thereto. The first medical image and the orientation information of the probe 111 may be received by a single interface.

The user interface 330 receives an input for manipulating the registration apparatus 140 from the user, and outputs the first medical image, the second medical image, or a registered medical image obtained by the registration apparatus 140. The user interface 330 may include buttons, a keypad, a switch, dials, or a touch interface by which the user may directly manipulate the registration apparatus 140. The user interface 330 may include a display unit for displaying an image, and may include a touchscreen. According to another exemplary embodiment, the user interface 330 may include an input/output (I/O) port for connecting human interface devices (HIDs). The user interface 330 may include an I/O port for inputting or outputting an image.

The image processing unit 340 may output to the user interface 330 a registered image that is obtained by registering the first medical image and the second medical image that corresponds to the first medical image. The image processing unit 340 may include a first sub-object extracting unit 341 (e.g., first sub-object extractor) that extracts a first sub-object for registration from the first medical image, a second sub-object extracting unit 342 (e.g., second sub-object extractor) that extracts a second sub-object for registration from the second medical image, a calculation unit 343 (e.g., calculator) that calculates a conversion relationship between the first medical image and the second medical image based on aligning the first sub-object and the second sub-object, and an image extracting unit 344 (e.g., image extractor) that extracts from the second medical image a cross-section of the second medical image corresponding to a cross-section of the first medical image. The first sub-object and the second sub-object may be the same sub-object or may be different from each other. A method of calculating the conversion relationship may vary according to whether the first and second sub-objects are the same or different from each other.

The first sub-object extracting unit 341 may extract the first sub-object from the first medical image. The first sub-object may be a sub-object that is clearly shown in the first medical image. For example, when the first medical image is an ultrasound image including a liver, the first sub-object may be an inferior vena cava (IVC) or a diaphragm that is disposed adjacent to the liver as well as the liver. Alternatively, the first sub-object may be at least one selected from a kidney, a gall bladder, a portal vein, a hepatic vein, and the IVC that are disposed adjacent to the liver. Alternatively, when an organ of interest is a heart, the first sub-object may be at least one selected from the IVC, the liver, the gall bladder, a spleen, and a renal vein that are disposed adjacent to the heart. When the organ of interest is a thyroid, the first sub-object may be at least one selected from a carotid and a jugular vein that are disposed adjacent to the thyroid. When the organ of interest is a pancreas, the first sub-object may be at least one selected from the IVC, a splenic vein, a splenic artery, and the spleen that are disposed adjacent to the pancreas.

The second sub-object extracting unit 342 may extract the second sub-object from the second medical image. The second sub-object may be the same as or different from the first sub-object. When the organ of interest is the liver, the diaphragm and the IVC may be clearly shown in both the first medical image that is an ultrasound image and the second medical image that is an MR image. Accordingly, the first and second sub-object extracting units 341 and 342 may respectively extract the diaphragm or the IVC as the first and second sub-objects. However, the exemplary embodiments are not limited thereto. The second sub-object extracting unit 342 may extract the second sub-object that is different from the first sub-object and is disposed adjacent to the first sub-object. For example, when the first sub-object is the diaphragm, the second sub-object may be the liver. In this case, although the liver and the diaphragm are not the same sub-object, since a boundary line of the liver and the diaphragm contact each other, the first and second medical images may be registered by considering the diaphragm as the boundary line of the liver and aligning the diaphragm and the liver.

The calculation unit 343 may calculate a conversion relationship between the first medical image and the second medical image by aligning the first sub-object and the second sub-object. When the first sub-object and the second sub-object are the same, the calculation unit 343 may calculate the conversion relationship between the first medical image and the second medical image by matching the first sub-object and the second sub-object. However, when the first sub-object and the second sub-object are different from each other, the calculation unit 343 may calculate the conversion relationship between the first medical image and the second medical image by matching a geometric arrangement between the first sub-object and the second sub-object with a geometric arrangement that is previously stored. The geometric arrangement between the first sub-object and the second sub-object may be previously stored.

For example, the calculation unit 343 may calculate a conversion relationship between a coordinate system of the first medical image and a coordinate system of the second medical image by rotating a coordinate axis of the first medical image to be parallel to a reference axis and moving the rotated coordinate axis of the first medical image to align the first sub-object and the second sub-object. The movement may include any one of a rotation and a linear movement. As described above, when the conversion relationship between the coordinate system of the first medical image and the coordinate system of the second medical image is calculated by using the reference axis, the calculation may be more easily performed than when the conversion relationship between the coordinate systems is calculated based on an arbitrary point.

The image extracting unit 344 may extract from the second medical image a cross-section of the second medical image corresponding to a cross-section of the first medical image that is received from the first medical apparatus 110. For example, the image extracting unit 344 may convert coordinate information about the cross-section of the first medical image into coordinate information in the second medical image by using the conversion relationship, and may extract from the second medical image the cross-section of the second medical image having the conversion-obtained coordinate information. The coordinate information about the cross-section of the first medical image may include orientation information and location information, and may be the same as coordinate information of the probe 111.

A detailed operation of the registration apparatus 140 will be explained below with reference to a method of registering medical images according to an exemplary embodiment. Although the particular elements of the registration apparatus 140 used to perform each process may not be specified in the below description, one of ordinary skill in the art would understand which elements may be used to perform the method from the above description.

Figure 4:
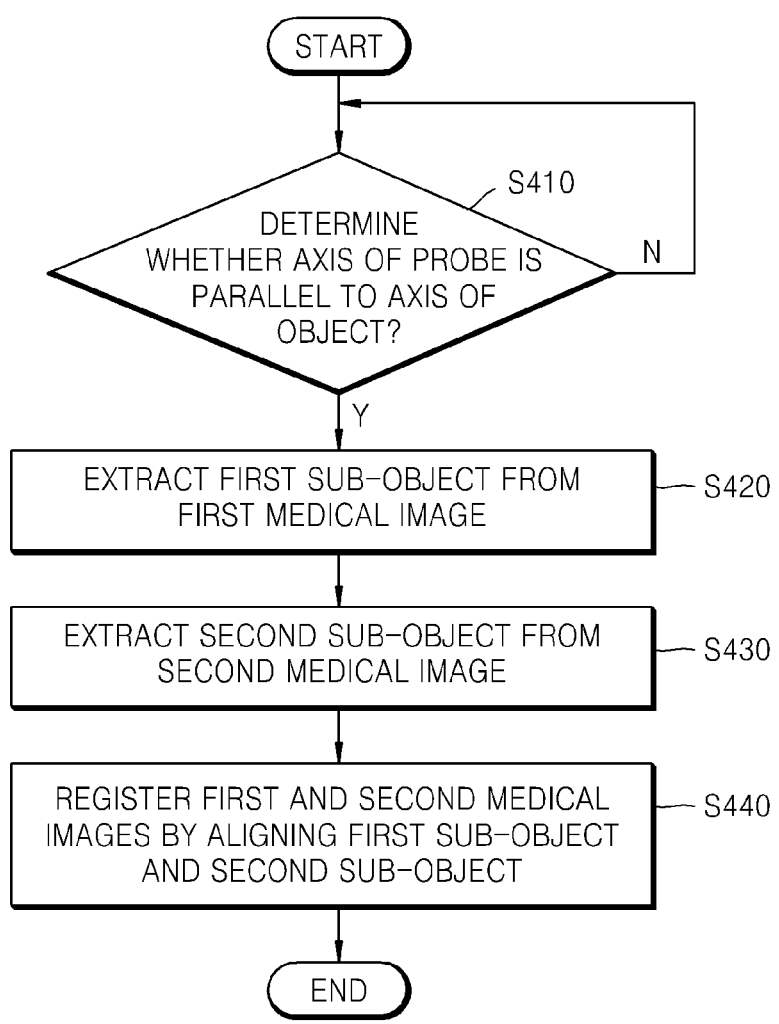
FIG. 4 is a flowchart illustrating a method of registering medical images, according to an exemplary embodiment.

FIG. 4 is a flowchart illustrating a method of registering medical images, according to an exemplary embodiment. Referring to FIG. 4, in operation S410, the control unit 350 determines whether an axis of the probe 111 is disposed to be parallel to an axis of an object. A user may dispose the axis of the probe 111 to be parallel to the axis of the object in a state where the probe 111 is placed on the object. When the axis of the probe 111 is disposed to be parallel to the axis of the object, the user may input a user command indicating that the axis of the probe 111 has been disposed to be parallel to the axis of the object. As a result of the input command, the control unit 350 may determine that the axis of the probe 111 is disposed to be parallel to the axis of the object, and may set the axis of the probe 111 as a reference axis. In addition, the detection apparatus 130 may set the axis of the probe 111 as a coordinate axis of a coordinate system used by the detection apparatus 130. The axis of the object may be parallel to a coordinate axis used in a second medical image.

When the axis of the probe 111 is disposed to be parallel to the axis of the object, the method proceeds to operation S420. In operation S420, the first sub-object extracting unit 341 may extract a first sub-object from a first medical image. The first medical apparatus 110 may obtain a cross-section of the first medical image by using the probe 111 in real time, and may generate the first medical image that is a 3D image by reconstructing the cross-section of the first medical image. The first medical apparatus 110 may apply (e.g., transmit) the first medical image to the registration apparatus 140, and the first sub-object extracting unit 341 of the registration apparatus 140 may extract the first sub-object from the first medical image.

To extract the first sub-object, the first sub-object extracting unit 341 may use a brightness value. For example, information about a brightness value range, and a shape, a diameter, and a length of an IVC in a B-mode image according to ultrasound reflection characteristics of the IVC may be previously stored in the registration apparatus 140. The first sub-object extracting unit 341 may determine a critical brightness value for binarizing the first medical image by using the previously stored information. The critical brightness value that is a basis for binarizing the first medical image may be determined according to ultrasound reflection characteristics of a sub-object to be extracted. The first sub-object extracting unit 341 may extract an area corresponding to the IVC from the first medical image that is binarized by using the information about the shape, the diameter, and the length. It will be understood that the first sub-object extracting unit 341 may perform extraction by using any of various types of other methods.

In addition, in operation S430, the second sub-object extracting unit 342 may extract a second sub-object from the second medical image. The second sub-object may be the same as the first sub-object, or may be different from the first sub-object. A method of extracting the second sub-object may be the same as a method of extracting the first sub-object or may be different. The second sub-object extracting unit 342 may previously extract the second sub-object from the second medical image and may store the second sub-object. Accordingly, the second sub-object extracting unit 342 may load the second sub-object that is previously stored.

In operation S440, the registration apparatus 140 may register the first and second medical images by aligning the first and second sub-objects. The registration apparatus 140 may calculate a conversion relationship between a coordinate system of the first medical image and a coordinate system of the second medical image based on aligning the first and second sub-objects.

Figure 5:
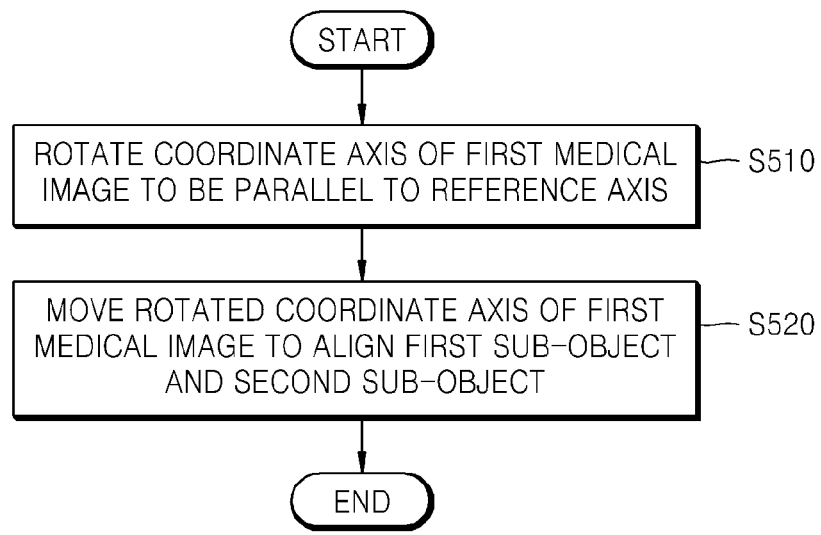
FIG. 5 is a flowchart illustrating a method of calculating a conversion relationship between a coordinate system of a first medical image and a coordinate system of a second medical image, according to an exemplary embodiment.

FIG. 5 is a flowchart illustrating a method of calculating a conversion relationship between a coordinate system of a first medical image and a coordinate system of a second medical image, according to an exemplary embodiment. Referring to FIG. 5, in operation S510, the calculation unit 343 rotates a coordinate axis of the first medical image to be parallel to a reference axis. The first medical apparatus 110 may obtain the first medical image that is a 3D image by sweeping the probe 111. Since the coordinate axis of the first medical image may be or not be parallel to the reference axis, the calculation unit 343 may rotate the coordinate axis of the first medical image to be parallel to the reference axis.

In operation S520, the calculation unit 343 aligns a first sub-object and a second sub-object by moving the rotated coordinate axis of the first medical image. The alignment between the first sub-object and the second sub-object may vary according to whether the first and second sub-objects are the same or not.

Figure 6:
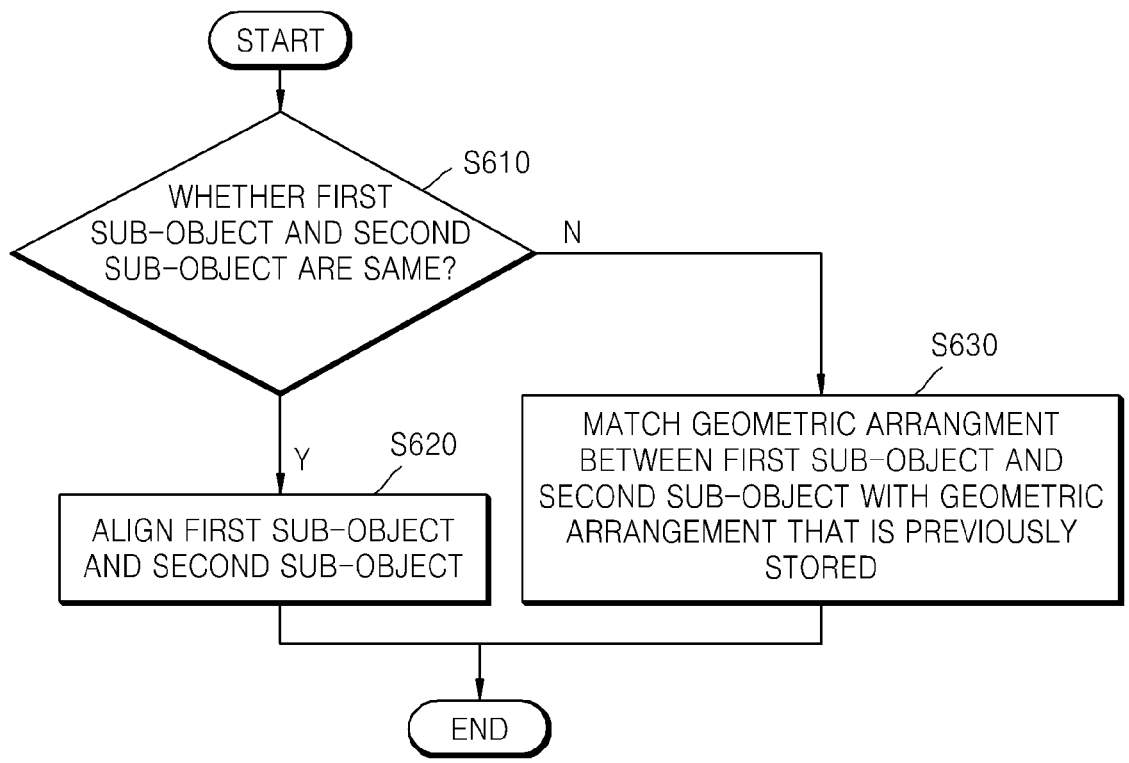
FIG. 6 is a flowchart illustrating a method of aligning a first sub-object and a second sub-object, according to an exemplary embodiment.

FIG. 6 is a flowchart illustrating a method of aligning first and second sub-objects, according to an exemplary embodiment. In operation S610, the calculation unit 343 determines whether the first sub-object and the second sub-object are the same. The calculation unit 343 may determine whether the first and second sub-objects are the same in consideration of a size and a radius of each of the first and second sub-objects. Alternatively, since the second sub-object may be previously extracted and stored, the first sub-object extracting unit 341 may load information about the second sub-object and may extract the first sub-object that is the same as the second sub-object by using the loaded information. In this case, the calculation unit 343 may determine that the first and second sub-objects are the same. Also, since different sub-objects may be clearly shown in a first medical image and a second medical image, information about each of the first and second sub-objects to be extracted may be stored in the registration apparatus 140. When the first and second sub-objects are different from each other, information about a geometric arrangement between the first and second sub-objects may be previously stored in the registration apparatus 140.

When the first and second sub-objects are the same, the method proceeds to operation S620. In operation S620, the calculation unit 343 may align the first sub-object and the second sub-object by moving a rotated coordinate axis of the first medical image to match the first sub-object and the second sub-object. In contrast, when the first and second sub-objects are different from each other, the method proceeds to operation S630. In operation S630, the calculation unit 343 may align the first sub-object and the second sub-object by moving the rotated coordinate axis of the first medical image to match a geometric arrangement between the first and second sub-objects with a geometric arrangement that is previously stored. The movement of the coordinate axis may include at least one selected from a rotation and a linear movement. Since the coordinate axis of the first medical image is rotated to be parallel to a reference axis, a rotation range of the coordinate axis of the first medical image that is rotated to align the first sub-object and the second sub-object is small. Accordingly, fewer errors may occur than when the coordinate axis of the first medical image is changed in an arbitrary direction.

Accordingly, the calculation unit 343 may calculate a conversion relationship between a coordinate system of the first medical image and a coordinate system of the second medical image by rotating and moving the coordinate axis of the first medical image according to Equation 1:

$$T = x_{MR,0} x_{US,0}^{-1} \qquad \text{Equation (1).}$$

In Equation 1, $x_{US,0}$ is coordinate information of the first sub-object in the coordinate system of the first medical image, $x_{MR,0}$ is coordinate information of the second sub-object in the coordinate system of the second medical image, and T is a conversion relationship. The registration apparatus 140 may convert coordinate information about a cross-section of the first medical image in the coordinate system of the first medical image into coordinate information in the second medical image. The coordinate system used in the first medical image and a coordinate system used by the detection apparatus 130 may be the same.

Figure 7:
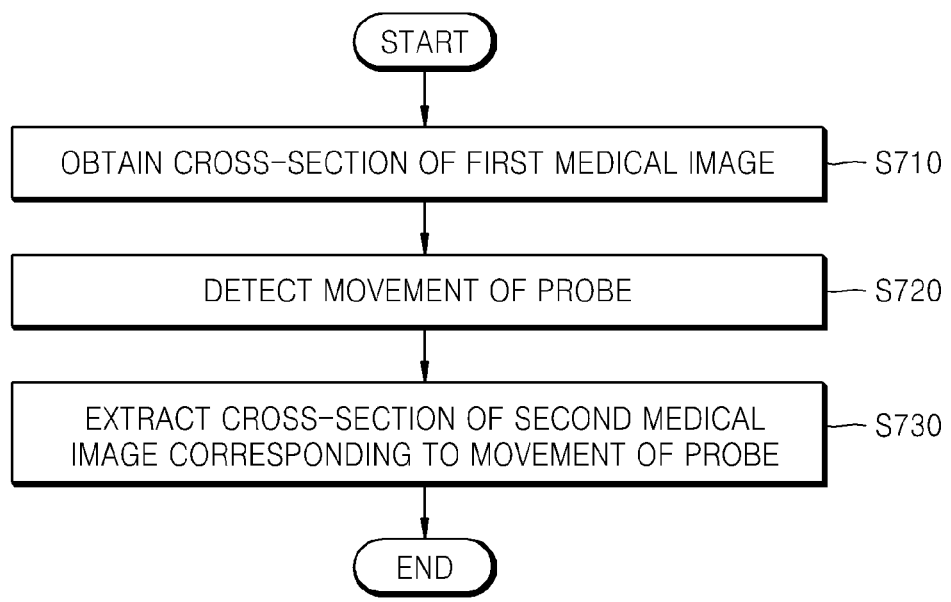
FIG. 7 is a flowchart illustrating a method of extracting a cross-section of the second medical image corresponding to a cross-section of the first medical image, according to an exemplary embodiment.

FIG. 7 is a flowchart illustrating a method of extracting a cross-section of a second medical image corresponding to a cross-section of a first medical image, according to an exemplary embodiment. Referring to FIG. 7, in operation S710, the first medical apparatus 110 may obtain in real time the cross-section of the first medical image by using the probe 111. When the first medical apparatus 110 is an ultrasonography machine, the first medical apparatus 110 may generate an ultrasound image by emitting ultrasound to an object by using the probe 111 and detecting reflected ultrasound. The obtained first medical image is applied to the registration apparatus 140.

In operation S720, the detection apparatus 130 may detect a movement of the probe 111. As the probe 111 moves, a location and an orientation of the ultrasound that is emitted to the object may be changed, and a view of the first medical image may also be changed. Since coordinate information indicating a location and an orientation of the probe 111 and a view of the first medical image correspond to each other in a one-to-one manner, once the movement of the probe 111 is detected, the view of the first medical image may be predicted. Although the obtaining of the first medical image and the detection of the movement of the probe may be performed simultaneously, the obtaining of the first medical image has been first described for convenience of explanation.

In operation S730, the registration apparatus 140 may extract from the second medical image the cross-section of the second medical image corresponding to the movement of the probe 111. The second medical image may be an image that is previously captured. Shapes of an organ and a lesion may be more clearly shown in the second medical image than in the first medical image. The second medical image may be received from the second medical apparatus 120, and may be a stored image. For example, the second medical image may be a CT image or an MR image. In detail, when at least one selected from a location and an orientation of the probe 111 is changed according to at least one selected from a movement and a rotation of the probe 111, the detection apparatus 130 may re-detect coordinate information of the probe 111, and may apply (e.g., transmit) the re-detected coordinate information of the probe 111 to the registration apparatus 140. Since coordinate information of the probe 111 is coordinate information about the cross-section of the first medical image, the calculation unit 343 may convert re-detected coordinate information $x_{US,t}$ about the cross-section of the first medical image into coordinate information $x_{MR,t}$ in the coordinate system of the second medical image by using a conversion relationship T according to Equation 2:

$$x_{MR,t} = Tx_{US,t} \qquad \text{Equation (2).}$$

The image extracting unit 344 may extract the cross-section having the conversion-obtained coordinate information from the second medical image. The cross-section of the first medical image and the cross-section of the second medical image may correspond to the same view of the object. The cross-section of the first medical image and the cross-section of the second medical image corresponding to the cross-section of the first medical image may be displayed on the display apparatus 150 via the user interface 330 to the outside. The cross-section of the first medical image and the cross-section of the second medical image corresponding to the cross-section of the first medical image may be displayed at different areas on one screen or may be displayed on one area by being shown as overlapping with each other.

Since the reference axis is set and then the conversion relationship between the coordinate system of the first medical image and the coordinate system of the second medical image is calculated by using the reference axis, image registration may be more easily performed and fewer errors may occur than when a plurality of images having different modalities are registered in an arbitrary direction and at an arbitrary point.

The afore-described exemplary embodiments may be implemented as an executable program, and may be executed by a general-purpose digital computer that runs the program by using a computer-readable recording medium. Examples of the computer-readable medium include storage media such as magnetic storage media (e.g., read-only memories (ROMs), floppy discs, or hard discs), optically readable media (e.g., compact disk-read only memories (CD-ROMs), or DVDs), etc.

While the exemplary embodiments have been particularly shown and described with reference to certain exemplary embodiments thereof by using specific terms, the exemplary embodiments and terms have merely been used to explain aspects of the exemplary embodiments and should not be construed as limiting the scope of the exemplary embodiments as defined by the claims. The exemplary embodiments should be considered in a descriptive sense only and not for purposes of limitation. Therefore, the scope of the exemplary embodiments is defined not by the detailed description of the exemplary embodiments but by the appended claims, and all differences within the scope will be construed as being included in the exemplary embodiments.

What is claimed is:

1. A method of registering medical images, the method comprising:
    in response to a user command indicating that an axis of a probe is parallel to a an axis of an object, setting the axis of the probe as a reference axis and a coordinate axis of a coordinate system used by a detection apparatus;
    extracting a first sub-object from a first medical image that includes the object and is obtained by using the probe, the first medical image being of a first modality;
    extracting a second sub-object from a second medical image that includes the object, the second medical image being of a second modality that is different from the first modality, an axis of the second medical image being parallel to the axis of the object; and
    in response to the first sub-object and the second sub-object representing different physical objects, registering the first medical image and the second medical image by determining a boundary line of the second sub-object as the first sub-object, and aligning the first sub-object and the second sub-object about the reference axis;
    wherein the registering comprises calculating a conversion relationship between a coordinate system of the first medical image and a coordinate system of the second medical image based on aligning the first sub-object and the second sub-object;
    wherein the calculating of the conversion relationship comprises rotating a coordinate axis of the first medical image to be parallel to the reference axis and moving the rotated coordinate axis of the first medical image to align the first sub-object with the second sub-object, wherein the moving the rotated coordinate axis includes at least one of a rotation and a linear movement; and
    wherein the aligning comprises matching a geometric arrangement between the first sub-object and the second sub-object with a geometric arrangement that is previously stored.

2. The method of claim 1, further comprising extracting from the second medical image a cross-section of the second medical image corresponding to a cross-section of the first medical image based on the conversion relationship.

3. The method of claim 2, wherein the extracting of the cross-section of the second medical image corresponding to the cross-section of the first medical image comprises:
    converting coordinate information about the cross-section of the first medical image into coordinate information of the second medical image to generate conversion-obtained coordinate information; and
    extracting from the second medical image the cross-section of the second medical image having the conversion-obtained coordinate information.

4. The method of claim 3, wherein the coordinate information about the cross-section of the first medical image corresponds to coordinate information of the probe in a one-to-one manner.

5. The method of claim 1, further comprising displaying both the first medical image and the second medical image on a same screen,
    wherein the first sub-object in the first medical image and the second sub-object in the second medical image are displayed to be aligned about the reference axis.

6. The method of claim 2, wherein the cross-section of the first medical image and the cross-section of the second medical image correspond to a same view of the object.

7. The method of claim 1, wherein the registering comprises:
    in response to the first sub-object and the second sub-object representing a same physical object, registering the first medical image and the second medical image by aligning the first sub-object and the second sub-object about the reference axis, and by matching the first sub-object and the second sub-object.

8. The method of claim 1, wherein the first medical image is an image that is captured in real time, and the second medical image is an image that is previously captured.

9. The method of claim 1, wherein the first medical image is at least one of an ultrasound image and an optical coherence tomography (OCT) image, and the second medical image is at least one of a magnetic resonance (MR) image, a computed tomography (CT) image, a position emission tomography (PET) image, a single-photon emission computed tomography (SPECT) image, and an X-ray image.

* * * * *